(12) United States Patent  (10) Patent No.: US 7,544,170 B2
Williams et al.  (45) Date of Patent: Jun. 9, 2009

(54) GUIDEWIRE MANAGEMENT DEVICES AND METHODS

(75) Inventors: Eric Williams, Fairfield, CA (US); John H. Ream, San Jose, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 459 days.

(21) Appl. No.: 10/420,770

(22) Filed: Apr. 23, 2003

(65) Prior Publication Data

US 2004/0019302 A1 Jan. 29, 2004

Related U.S. Application Data

(60) Provisional application No. 60/375,075, filed on Apr. 25, 2002.

(51) Int. Cl.
*A61B 5/00* (2006.01)
(52) U.S. Cl. .................... 600/585; 604/159; 220/120
(58) Field of Classification Search ......... 600/433–435, 600/585; 604/159, 528; 606/108; 226/120, 226/127, 129
See application file for complete search history.

(56) References Cited

U.S. PATENT DOCUMENTS

| 2,625,934 | A | * | 1/1953 | Halliday | 606/200 |
|---|---|---|---|---|---|
| 3,561,445 | A | * | 2/1971 | Katerndahl et al. | 604/159 |
| 4,637,404 | A | * | 1/1987 | Gessman | 607/126 |
| 4,688,709 | A | * | 8/1987 | Minor | 226/128 |
| 4,860,757 | A | * | 8/1989 | Lynch et al. | 600/434 |
| 5,125,416 | A | * | 6/1992 | Phillips | 600/585 |
| 5,350,101 | A | * | 9/1994 | Godlewski | 226/129 |
| 5,579,780 | A | * | 12/1996 | Zadini et al. | 600/585 |
| 5,797,858 | A | * | 8/1998 | Rourke | 600/585 |
| 5,827,202 | A | * | 10/1998 | Miraki et al. | 600/585 |
| 5,868,755 | A | * | 2/1999 | Kanner et al. | 606/108 |
| 5,944,701 | A | | 8/1999 | Dubrul | |
| 6,231,564 | B1 | * | 5/2001 | Gambale | 604/528 |
| 6,588,588 | B2 | * | 7/2003 | Samuels | 206/364 |
| 6,746,466 | B2 | | 6/2004 | Eidenschink et al. | |
| 6,916,293 | B2 | | 7/2005 | Hamilton | |
| 2003/0036712 | A1 | * | 2/2003 | Heh et al. | 600/585 |
| 2004/0019302 | A1 | | 1/2004 | Williams et al. | |
| 2004/0260205 | A1 | | 12/2004 | Boutillette et al. | |

* cited by examiner

*Primary Examiner*—Max Hindenburg
*Assistant Examiner*—Renee Danega
(74) *Attorney, Agent, or Firm*—Crompton Seager & Tufte

(57) ABSTRACT

A method of performing a medical procedure on a living body is provided. The method comprises inserting a leading end portion of a guidewire into the living body and advancing a trailing end portion of the guidewire into a container, the container being arranged to coil the trailing end portion of the guidewire as the trailing end portion is advanced into the container. The invention extends to an advancing device operable to cause a trailing end portion of a guidewire to advance into a container. The advancing device comprises a body, an engaging mechanism on the body, the engaging mechanism being arranged releasably to engage the guidewire and to move relative to the body while engaging the guidewire thereby to cause the guidewire to advance through the body.

12 Claims, 13 Drawing Sheets

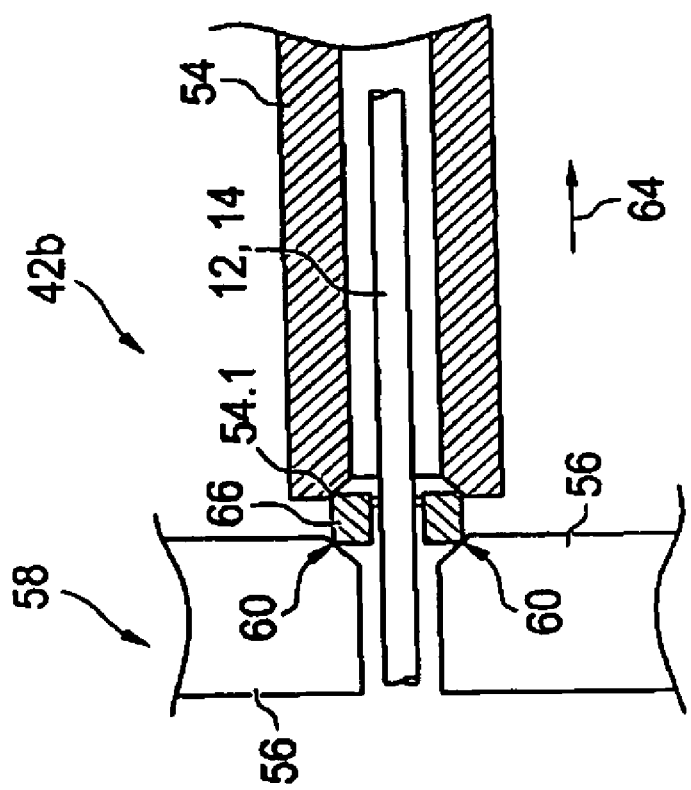
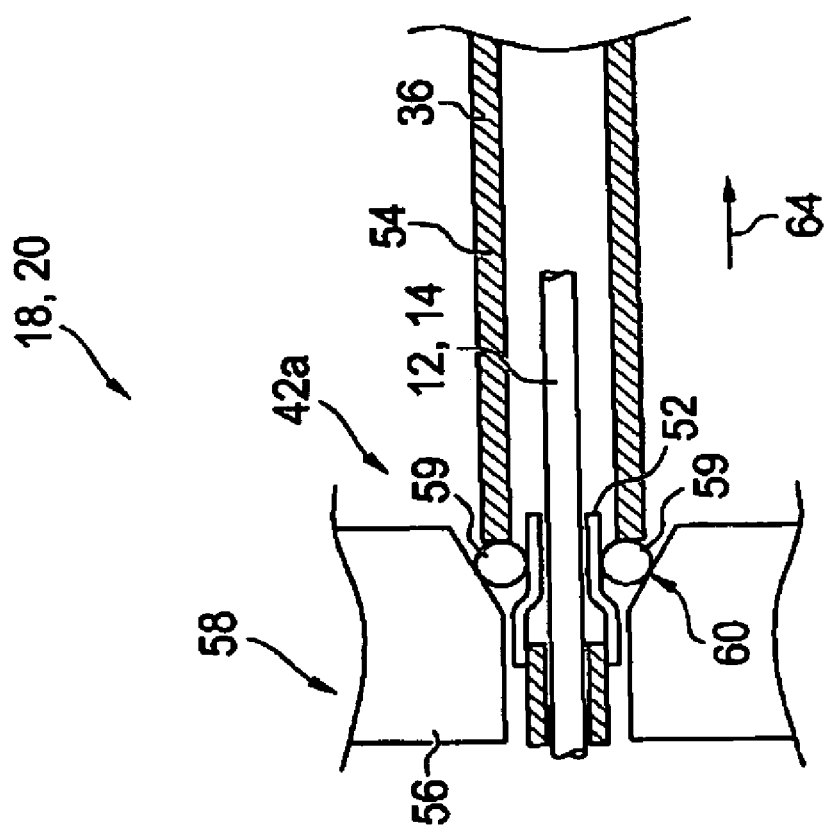

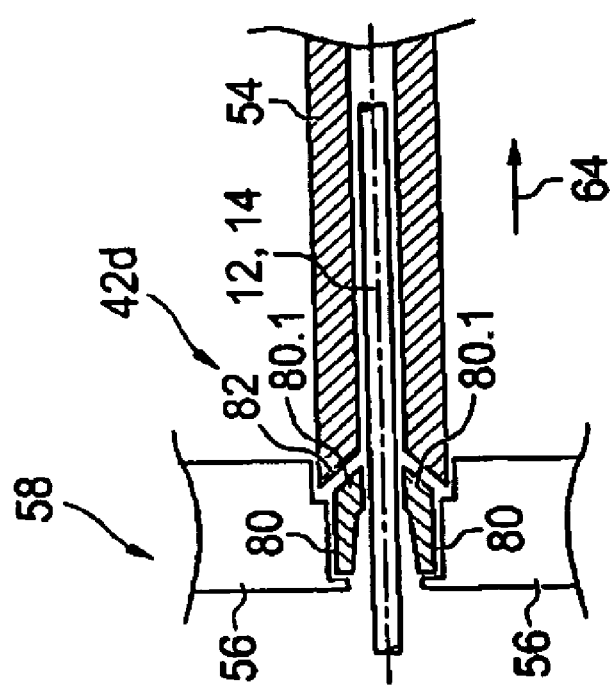
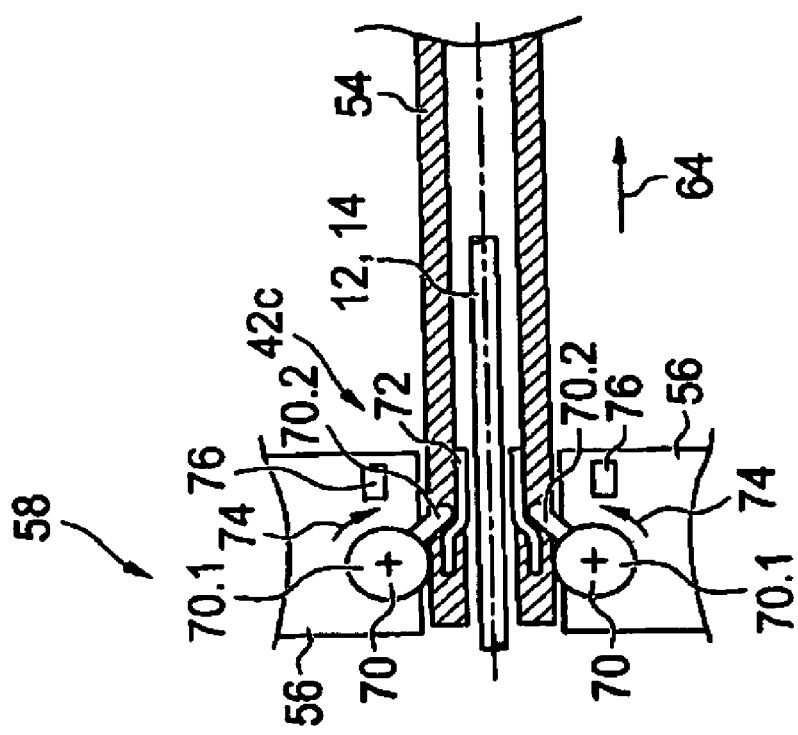

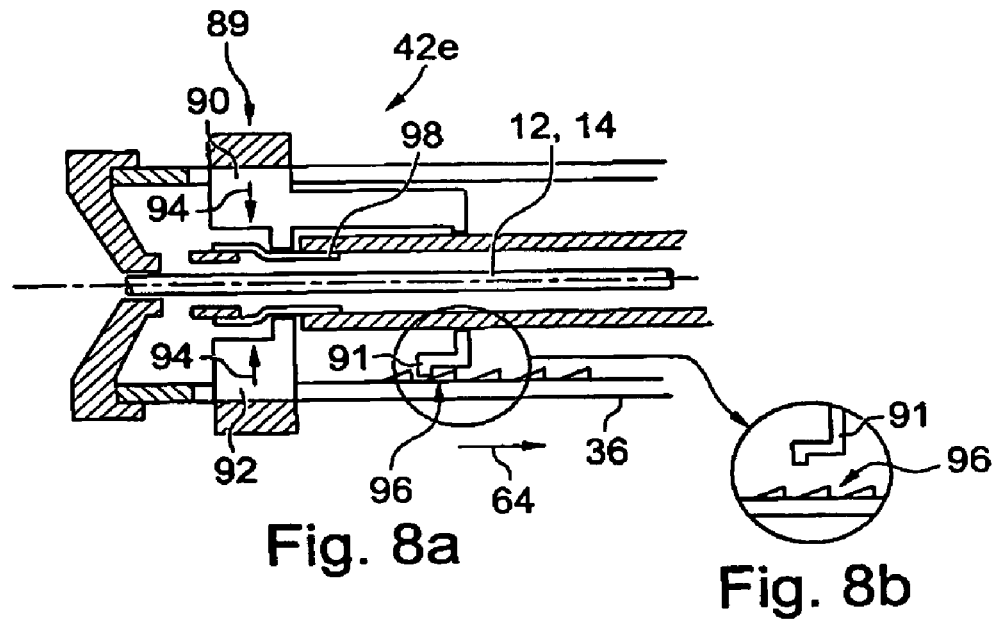
Fig. 8a
Fig. 8b
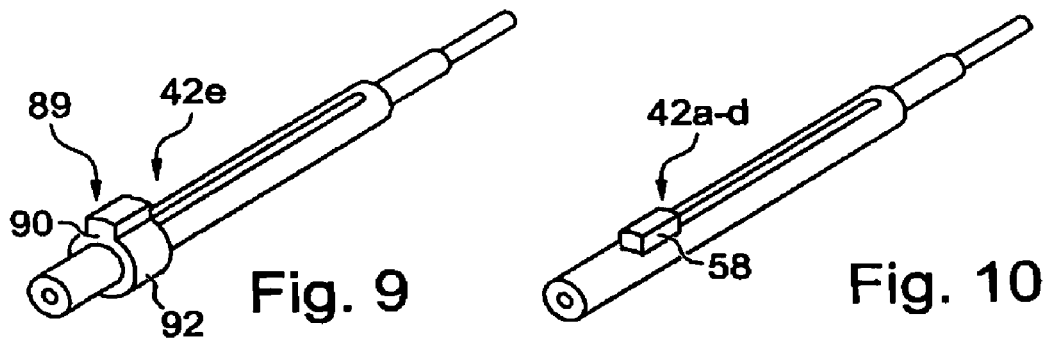
Fig. 9
Fig. 10
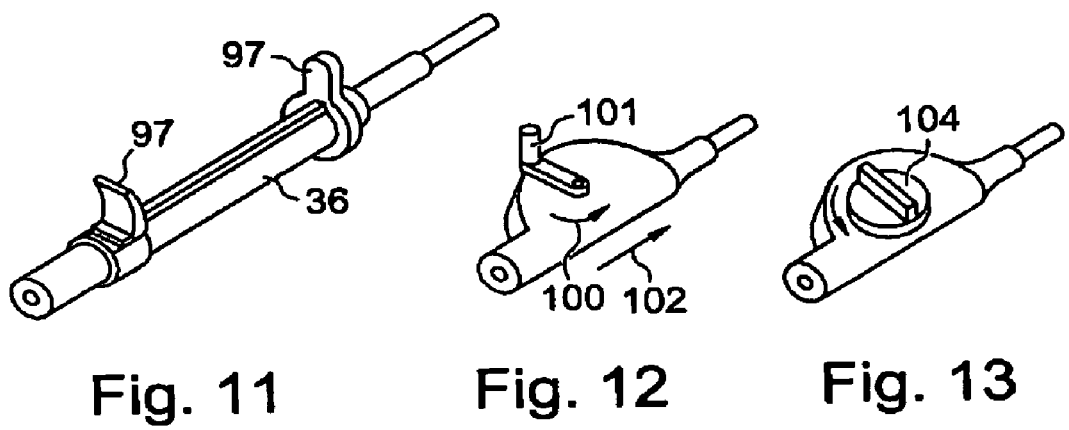
Fig. 11
Fig. 12
Fig. 13

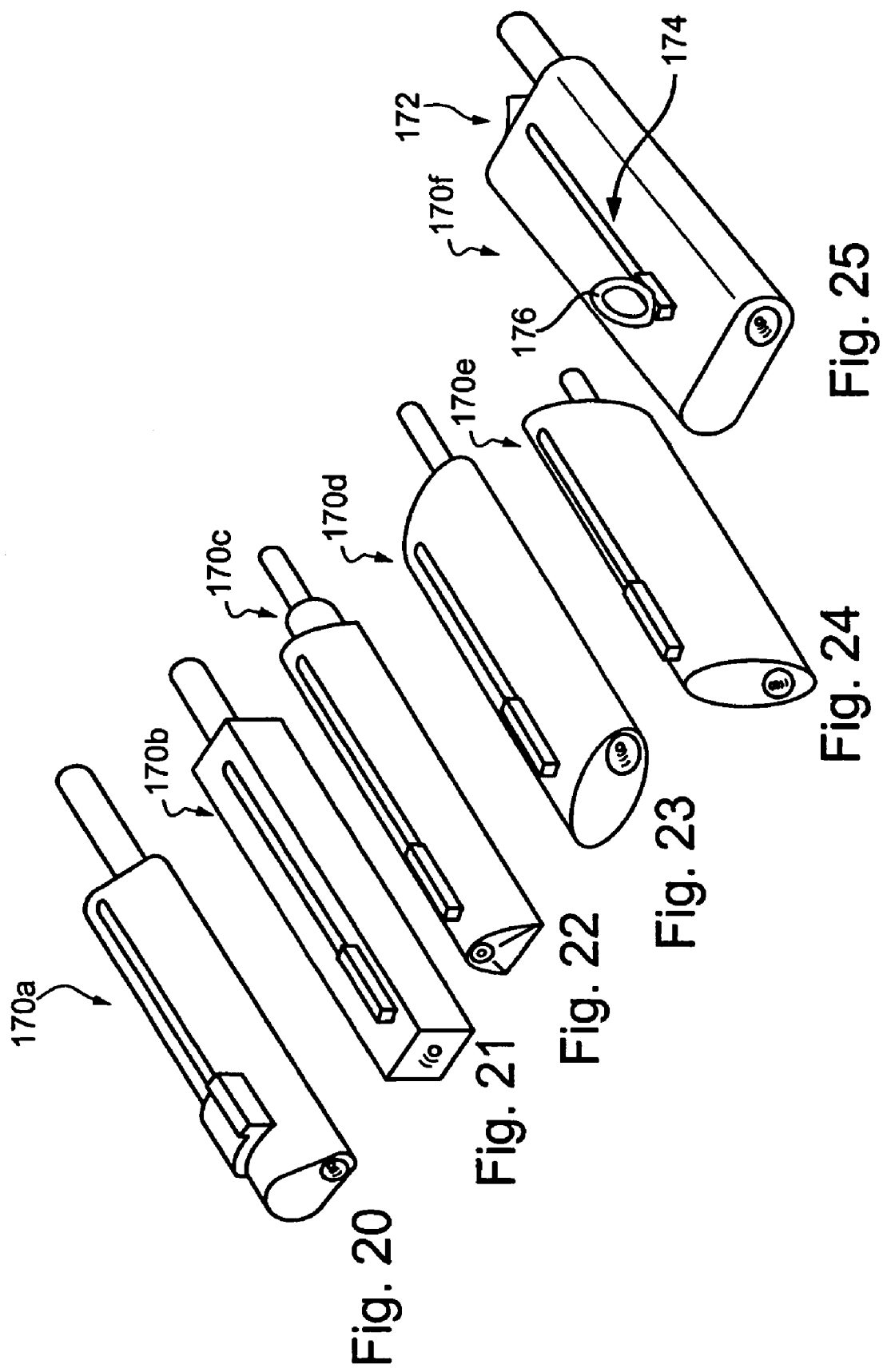

GUIDEWIRE MANAGEMENT DEVICES AND METHODS

CROSS-REFERENCE TO RELATED APPLICATIONS

This Application claims priority to U.S. Provisional Application No. 60/375,075, filed Apr. 25, 2002, the entire contents of which is hereby incorporated herein by reference in its entirety.

FIELD AND BACKGROUND OF THE INVENTION

The present invention relates to the field of guidewires and, more particularly, to positioning of guidewires in a living body.

Guidewires are often used in a variety of different medical procedures. For example, guidewires are used to position catheters in a lumen of a patient body, such as a patient's vasculature, bronchial branches, and the like, to facilitate stent deployment.

When guidewires are used in such medical procedures, a leading end portion of the guidewire is normally introduced into the patient's body through a naturally occurring orifice, or an incision, or the like. Where the guidewire is to be inserted into the patient's vasculature, for example, a hemostasis valve is used to block, or at least reduce, the flow of blood from the patient's vasculature. In such a case, the guidewire is typically introduced into the patient's vasculature through the hemostasis valve.

After having been introduced into the patient's body, the leading end portion of the guidewire is navigated through body lumens until a leading end of the guidewire is positioned at an area of interest. Navigation of the guidewire through the body lumen is often achieved by means of appropriate imaging techniques, such as fluoroscopy.

Naturally, the length of the guidewire to be introduced into the patient body to perform the medical procedure is determined by the distance between the point of entry, such as the hemostasis valve, and the area of interest, through the body lumens, or vasculature, between the point of entry and the area of interest. After a guidewire is appropriately positioned within the patient body, a trailing end portion of the guidewire typically extends out of the patient body from the point of entry. It has been found that the trailing end portion of the guidewire outside the patient body can be rather difficult to manage and can interfere with the efficiency by which the medical procedure to be performed is performed. This is especially true when more than one guidewire is being used during the medical procedure.

More than one guidewire is often used when, for example, stents are used to treat diseased vessels at or near a bifurcation (branch point) of a vessel. In such a case, the medical practitioner performing the medical procedure may confuse the trailing end portions of the guidewires protruding from the patient body with one another.

SUMMARY OF THE INVENTION

The invention relates to managing trailing end portions of guidewires while leading end portions of guidewires are positioned in a living body, such as a living body of a human patient, during a medical procedure. In particular, the invention relates to a method of performing a medical procedure on a living body and to an advancing device operable to cause a trailing end portion of a guidewire to advance into a container.

It has been found that guidewire management, in particular management of a trailing end portion, or where more than one guidewire is being used during a medical procedure, the management of a plurality of trailing end portions, would be beneficial to promote the efficacy by which such medical procedures are performed. Where more than one guide wire is being used simultaneously during a medical procedure confusion can arise in identifying which trailing end portion corresponds with which leading end portion. This is especially true if the trailing end portions become entwined, or entangled. Consequently, such confusion can unnecessarily prolong the time taken to perform the medical procedure. Yet further, should the wrong trailing end portion be manipulated, the efficiency whereby the medical procedure is performed can be further jeopardized.

Accordingly, it is an object of this invention to provide a method and devices for managing at least the trailing end portion of one guide wire during the performance of a medical procedure.

According to one aspect of the invention, there is provided a method of performing a medical procedure on a living body, the method comprising inserting a leading end portion of a guidewire into the living body and advancing a trailing end portion of the guidewire into a container, the container being arranged to coil the trailing end portion of the guidewire as the trailing end portion is advanced into the container.

According to another aspect of the invention, there is provided an advancing device operable to cause a trailing end portion of a guidewire to advance into a container, the advancing device comprising a body, an engaging mechanism on the body, the engaging mechanism being arranged releasably to engage the guidewire and to move relative to the body while engaging the guidewire thereby to cause the guidewire to advance through the body, and a mounting formation on the body, on which mounting formation a container, shaped to cause the guidewire to coil in response to the guidewire being advanced thereinto, is mountable, such that, in use, when the container is mounted on the body and the advancing device is operated to advance a guidewire through the body, the guidewire is caused to advance into the container so as to be coiled in the container.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 4 shows a schematic cross-sectional view of part of an engaging mechanism of an advancing device in accordance with the invention;

FIG. 5 shows a schematic cross-sectional view of part of an engaging mechanism of another advancing device in accordance with the invention;

FIG. 6 shows a schematic cross-sectional view of part of an engaging mechanism of another advancing device in accordance with the invention;

FIG. 7 shows a schematic cross-sectional view of part of an engaging mechanism of another advancing device in accordance with the invention;

FIG. 8A shows a schematic cross-sectional view of an engaging mechanism of yet another advancing device in accordance with the invention, the engaging mechanism being in an engaged condition in which it engages a guide wire;

FIG. 8B corresponds to FIG. 8A and shows part of the engaging mechanism when the engaging mechanism is in a disengaged condition in which it is disengaged from the guide wire;

FIGS. 9-13 show schematic three-dimensional views of different embodiments of an advancing device in accordance with the invention;

FIGS. 20-25 show schematic three-dimensional views of further embodiments of an advancing device in accordance with the invention;

DESCRIPTION OF THE PREFERRED EMBODIMENTS

Figure 1:
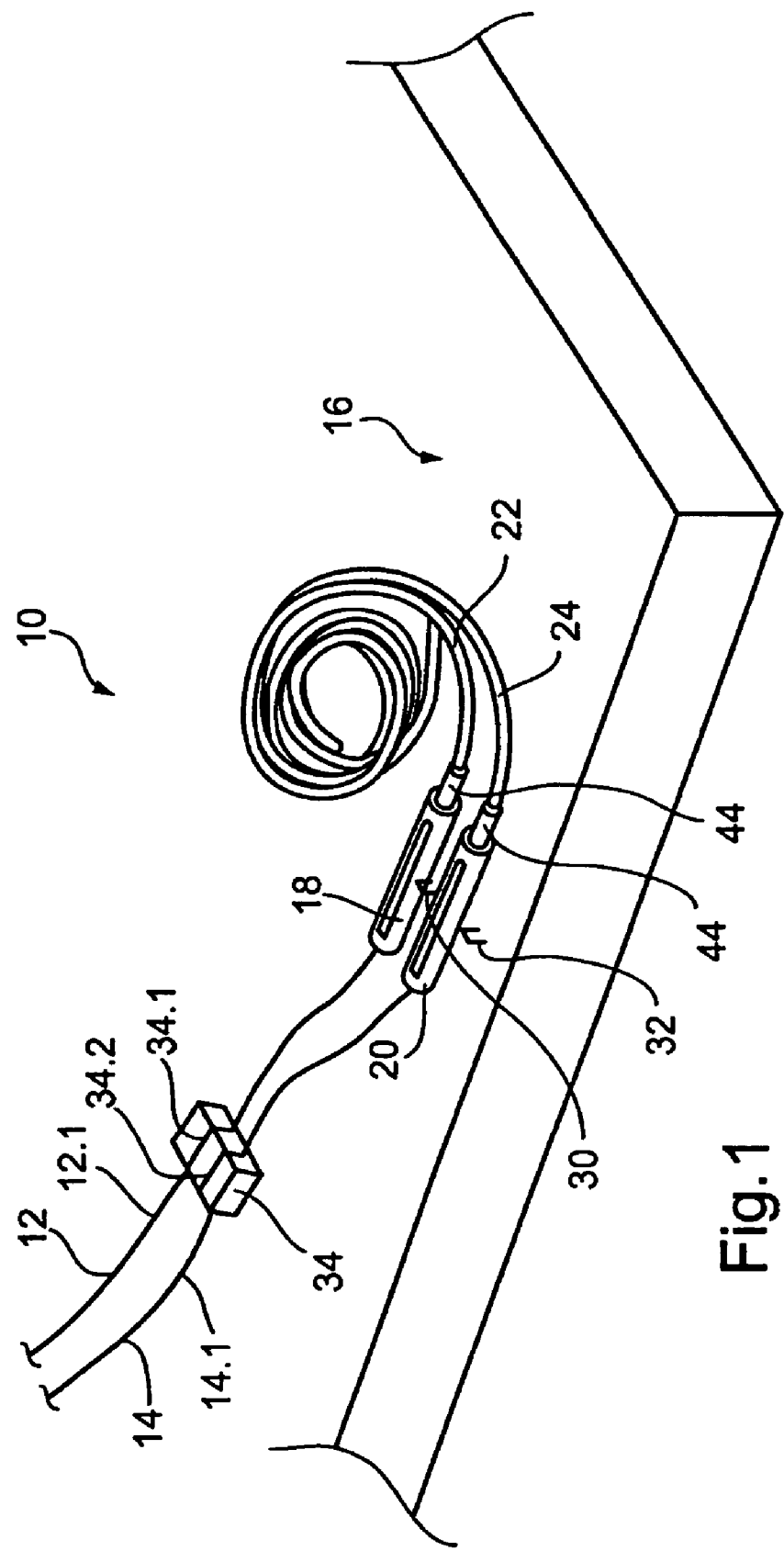
FIG. 1 shows a schematic three-dimensional view of trailing end portions of two guidewires being managed in accordance with a method of the invention using two advancing devices in accordance with the invention.

Referring to FIG. 1 of the drawings, a managing arrangement for managing the trailing end portions of two guidewires, in accordance with the invention, is generally indicated by reference numeral 10. The two guidewires are indicated by reference numerals 12 and 14, respectively. It will be understood that leading end portions (not shown) of the guidewires 12, 14 have been inserted into a patient body, trailing end portions 12.1, 14.1 of the guidewires 12, 14 being indicated in FIG. 1. Reference numeral 16 indicates a patient support, such as an operating table, or the like, on which the patient is supported.

As shown in FIG. 1, the management system 10 includes two advancing devices 18, 20, in accordance with the invention. Various alternative embodiments, of the advancing devices 18, 20, in accordance with the invention, will be described in greater detail herein below. Each of advancing devices 18 and 20 has a container mounted thereon. The containers are indicated at 22 and 24, respectively.

Guidewires are normally provided in prepackaged form. Normally, a guidewire is located within a sterile disposable protective loop within the package. Accordingly, when a guidewire is to be used to perform a medical procedure, the guidewire is normally removed from the package, and the sterile protective loop, so as to be inserted into a patient during a medical procedure. Conveniently, the containers 22, 24 can be the protective loops in which the guidewires 12, 14 are normally pre-packaged. In such a case, each advancing device 18, 20 has a mounting formation 44 on which end portions of such protective loops are releasably mountable, as indicated in FIG. 1.

However, it is to be appreciated that other suitable containers can be used, including containers dedicated for receiving the trailing end portions of the guide wires. In such a case, the containers can be connected to, or premounted on, the advancing device 18, 20. Advantageously, each advancing device 18, 20 can have an appropriate securing device 30, 32 for securing it to the support 16. The securing devices 30, 32 can be in the form of clamp arrangements so as to releasably clamp the devices 18, 20 to sheets, or the like, positioned on the support 16.

The system 10 can further include a guide arrangement 34 for locating the trailing end portions 12.1, 14.1 of the guidewires 12, 14 relative to each other and at a position between the patient and the devices 18, 20. The guide 34 can be in the form of a block having opposed slots 34.1, 34.2 for locating the guidewires 12, 14 therein while permitting axial movement of the guidewires within the slots 34.1, 34.2.

Figure 2:
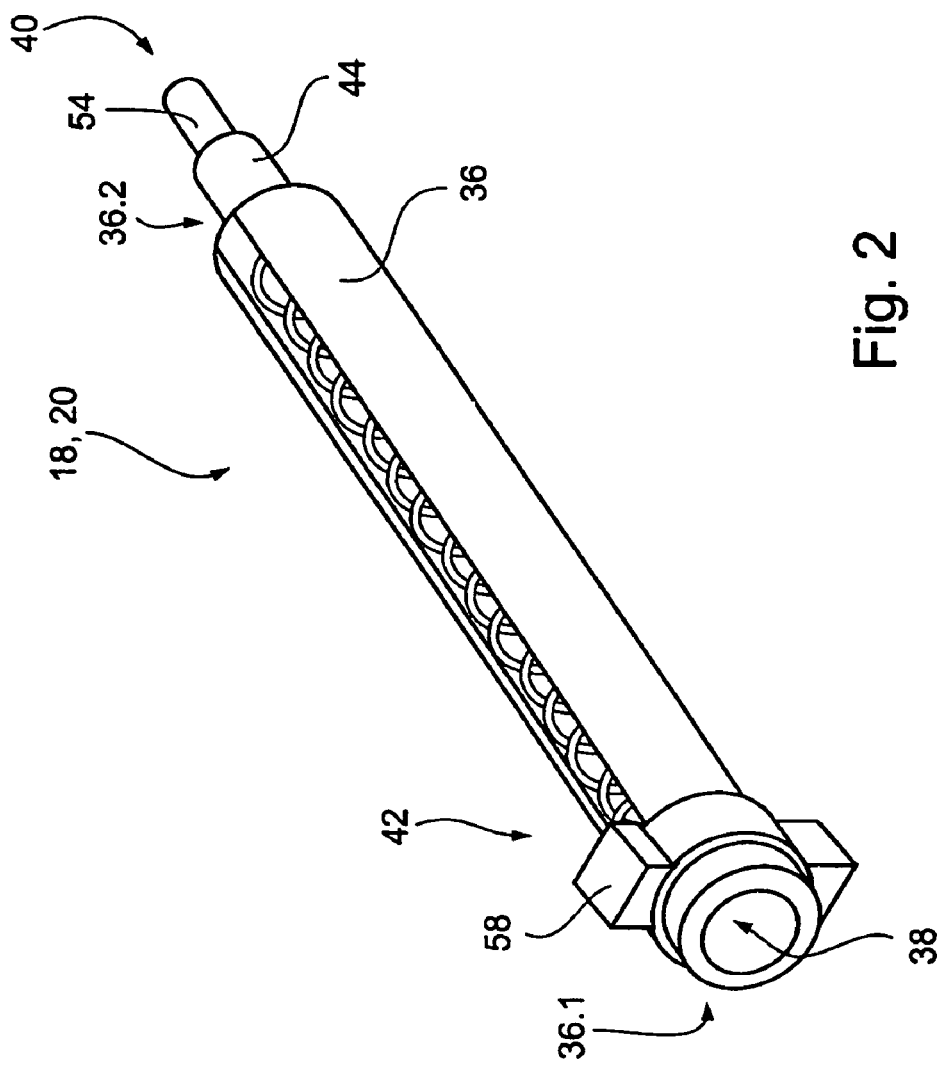
FIG. 2 shows a three-dimensional view of one embodiment of an advancing device in accordance with the invention.

Referring now to FIG. 2 of the drawings, one of the advancing devices 18, 20 is shown in greater detail. Each device 18, 20 includes an elongate body 36 defining an operatively forward end 36.1 and an operatively rearward end 36.2. At the forward end 36.1, an entry port 38 is defined. An exit port 40 is defined at the rearward end 36.2. In use, a trailing end of a trailing end portion of a guidewire is threaded into the entry port 38 so as to be positioned within the body 36. Each device 18, 20 further includes a guidewire engaging mechanism, generally indicated by reference numeral 42, for advancing the trailing end portion of the guidewire through the body 36 so as to exit the exit port 40. As mentioned, each device 18, 20 further includes a mounting formation 44 on which an end portion of one of the protective loops 22, 24 is releasably mountable. The mounting formation 44 can be of any appropriate form suitable for receiving an end portion of one of the protective loops 22, 24. Advantageously, the mounting formation 44 is arranged to receive end portions of protective loops having different internal dimensions. Accordingly, the formation 44 can have an outer surface which tapers radially inwardly in a direction away from the body 36. The formation 44 can be similar to a Luer type fitting, such as the Luer type fitting HNS/HIMA MD70-1-1983. The formation 44 can be of a resilient material, such as a natural rubber, a synthetic plastics material, a silicone based material, or the like. When one of the loops 22, 24 is mounted on the mounting formation 44, the guidewire, when advanced through the port 38, will be caused to advance through the body 36 and into the loop 22, 24 in response to an engaging mechanism 42 being operated, as described in further detail herein below.

Figure 3:
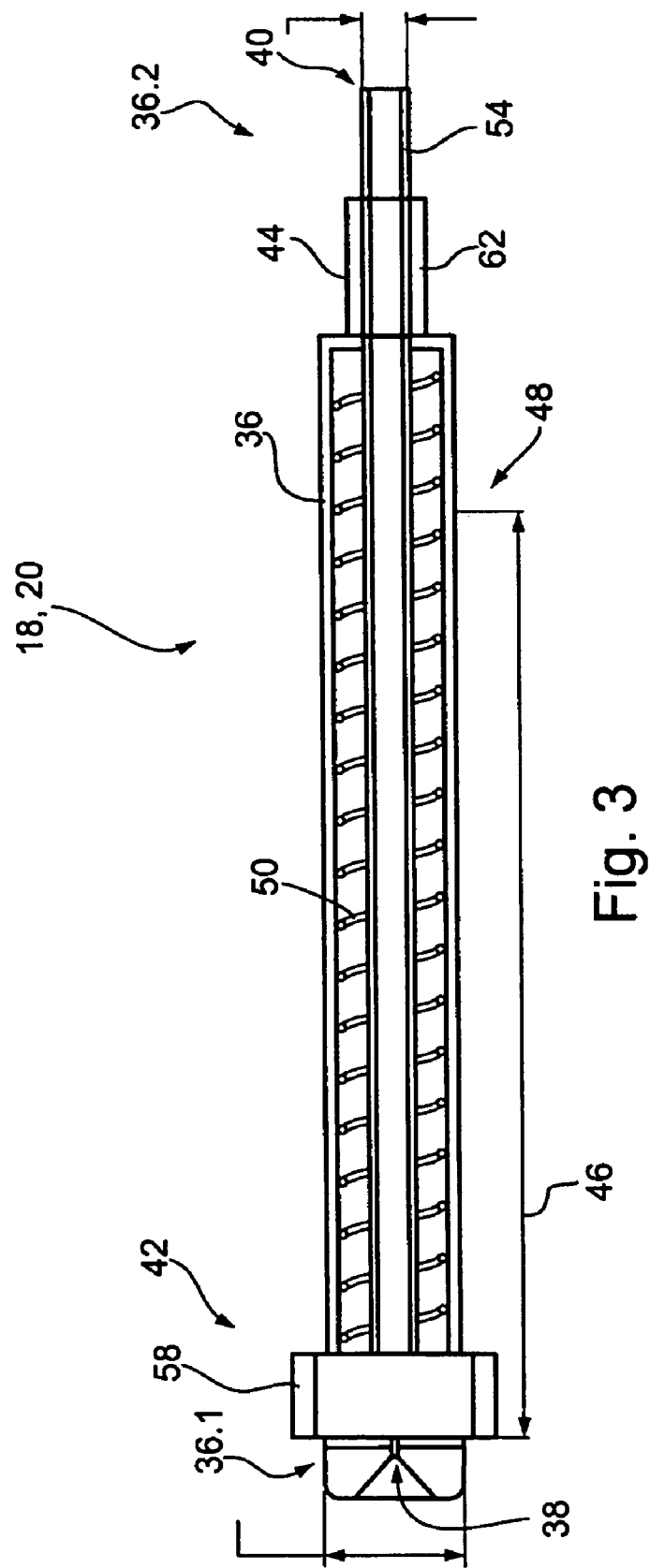
FIG. 3 shows a schematic cross-sectional side view of part of the advancing device shown in FIG. 2.

FIG. 3 shows a schematic cross-sectional view of the advancing device 18, 20, shown in FIG. 2. The engaging mechanism 42 is arranged to displace between an operatively forward position, as indicated in FIG. 3, and an operatively rearward position, as indicated at 48 and as indicated by arrow 46. After an end of the trailing end portion of the guidewire has been inserted through the entry port 38, and the engaging mechanism 42 is caused to displace to its operatively rearward position at 48, the engaging mechanism 42 automatically engages the guidewire and causes it to be advanced along the body 36, which has a forward end 36.1 and a rearward end 36.2. When the engaging mechanism 42 reaches the operatively rearward position 48 and is returned to its operatively forward position, the guidewire is automatically released. In this fashion, the guidewire is advanced in a stepwise fashion along the body 36 by a distance generally equal to a stroke of the engaging mechanism 42, typically of about 100 mm, as indicated by referenced numeral 46. Conveniently, a helical coil spring 50 is provided within the body 36. The spring 50 acts under compression so as automatically to urge the engaging mechanism 42 to its operatively forward position from its operatively rearward position. When the engaging mechanism 42 is displaced in a direction from its operatively rearward position 48 to its operatively forward position, the guidewire is automatically released. This will be described in further detail herein below. It will be understood that repetitive displacement of the engaging mechanism 42 causes the guidewire to perform sequential advancement steps along the body 36 so that it exits the exit port 40 and advances into the container, or protective loop, when mounted on the mounting formation 44.

When the engaging mechanism 42 is not being used to advance the guidewire through the body 36, the guidewire is in a disengaged condition thereby to permit a person performing the medical procedure to extend the guidewire from the device 18, 20 without interference.

Various embodiments of the engaging mechanism 42 will now be described with reference to FIGS. 4-8.

Referring to FIG. 4, the engaging mechanism 42A includes an engaging member 52. The engaging member 52 is typically in the form of a length of resiliently deformable tubing. The length of tubing can be of any appropriate resilient material such as silicone, or the like. The engaging mechanism further comprises a guide tube 54 and an actuator, part of which is indicated by reference numeral 56. The part of the actuator 56 shown in FIG. 4 is typically in the form of flange formations intruding into the body 36 through appropriate slots extends along the body 36, the rest of the actuator being indicated by reference numeral 58 in FIGS. 2 and 3. Engaging mechanism 42A further comprises opposed spheres, or balls, indicated at 59. The flange formations 56 have inclined surfaces, or edges, indicated at 60.

As can best be seen with reference to FIGS. 2 and 3, the guide tube 54 exits the body 36 at the mounting formation 44. The exit port 40 is defined at an outer end of the guide tube 54. Where the guide tube 54 exits the body 36 in the region of the mounting formation 44, it is held inside a tubular portion 62. The mounting formation 44 is defined on an external surface of the tubular portion 62. The guide tube 54 extends through the tubular portion 62 inside thereof. The passage of the tubular guide 54 through the tubular portion 62 is such as to impose friction on the guide tube 54 so as to provide a degree of resistance to displacement of the guide tube 54 through the tubular portion 62.

Returning now to FIG. 4, when the actuator 58 is caused to displace in a direction indicated by arrow 64, the frictional resistance of the guide tube 54 through the tubular portion 62, which is shown in FIG. 3, for example, causes the balls 59 to travel radially inwardly along the inclined surfaces or edges 60. In this manner, the engaging member 52 is caused to deform radially inwardly thereby to engage the guidewire 12, 14. Accordingly, the guidewire 12, 14 is engaged by the engaging member 52 in response to displacement of the actuator 58 in the direction of arrow 64. As the actuator 58 is advanced further, the guidewire 12, 14, is advanced internally along the body 36 of the device 18, 20.

It will be understood, and as can best be seen with reference to FIGS. 2 and 3, that the guide tube 54 is displaced internally along the container, or protective loop, when mounted on the mounting formation 44, in response to the actuator 58 and, engaging mechanism 42, being displaced rearwardly along the body 36. In this way, entry of the guidewire 12, 14 into the protective loop is assisted.

Referring now to FIG. 5, and in which like reference numerals are used to designate similar parts unless otherwise stated, another engaging mechanism is indicated generally by reference numeral 42B. The mechanism 42B has an engaging member for releasably engaging the guidewire 12, 14 as indicated at 66. Engaging member 66 is also in the form of a resiliently deformable tubular length. The guide tube 54 of FIG. 5 includes an inclined surface at 54.1. The inclined surface 54.1 of the guide tube 54 and the inclined surface, or edges 60, of the flanges 56 cooperate to cause inward radial deformation of the engaging member 66 in response to displacement of the actuator 58 in the direction of arrow 64. As in the case with the engaging mechanism 42A in FIG. 4, resistance on the guide tube 54 by its passage through the tubular portion 62 indicated in FIGS. 2 and 3, causes relative movement of the tube 54 toward the flanges 56 thereby to cause inward radial deformation of the member 66.

Referring now to FIG. 6, another engaging mechanism, indicated generally by reference numeral 42C, comprises opposed cam formations 70. The cam formations 70 are shown generally as having circular bodies 70.1 from which arm portions 70.2 extend. Instead of such cam arrangements, each cam 70 can be in the form of a generally lobe shaped cam, similar to those normally found on a cam shaft of an internal combustion engine, for example. The mechanism 42C includes a radially inwardly deformable resilient member 72 similar to the member 52 of FIG. 4. In use, when the actuator 58, having flanges 56, is displaced in the direction of arrow 64, the resistance of the guide tube 54 through the tubular portion 62, which is shown in FIG. 3, for example, causes the cam bodies 70 to displace angularly as indicated by arrows 74 so as to cause the member 72 to engage around the guidewire 12, 14. Stops 76 can be provided to inhibit the arms 70.2, 70.2 from displacing angularly in a direction opposed to that indicated by arrow 74 beyond a predetermined angle. It will be appreciated that on the return stroke of the actuator 58, the friction of the guide tube 54 causes the cam bodies 70 to displace angularly in a direction opposed to that indicated by arrow 74 so as to cause the member 72 to disengage from the guidewire 12, 14.

Referring now to FIG. 7, in which like reference numerals are used to designate similar parts unless otherwise stated, another embodiment of an engaging mechanism is generally indicated by reference numeral 42D. The engaging member of the mechanism 42D is in the form of a collet structure which defines a plurality of collet limbs 80. The collet limbs 80 are arranged to be resiliently displaceable radially inwardly. As in the case with the mechanism 42B of FIG. 5, the guide tube 54 defines an inclined surface at 82. When the actuator 58 is displaced in the direction of arrow 64, free ends, indicated at 80.1, of the collet limbs 80 ride against the inclined surface 82 to cause them resiliently to displace radially inwardly thereby to grip the guidewire 12, 14. When the engaging mechanism 42D is returned after an operatively rearward stroke the resistance on the guide tube 54 by the tubular portion 62, which is shown in FIG. 3, for example, causes the guide tube 54 to displace in a direction away from the actuator flanges 56 thereby to release the collet limbs 80 from around the guidewire 12, 14.

Referring now to FIG. 8A of the drawings, in which like reference numerals are used to designate similar parts unless otherwise stated, a further alternative arrangement of an engaging mechanism is generally indicated by reference numeral 42E. The mechanism 42E comprises an actuator, generally indicated by reference numeral 89, which comprises two diametrically opposed bodies 90, 92. To enable the actuator 89 to engage the guidewire 12, 14 the opposed portions 90, 92 of the actuator 89 are displaced radially inwardly relative to each other as indicated by arrows 94. When the portions 90, 92 are displaced in this fashion, an engaging member 98 in the form of a resiliently deformable tubular member is displaced radially inwardly to engage the guidewire 12, 14. When the mechanism 42E is then displaced in the direction of arrow 64, the guidewire 12, 14 is advanced along the body 36. The mechanism 42E further comprises a ratchet-like arrangement 96. The ratchet-like arrangement 96 is structured to enable the mechanism 42E to travel in the direction of arrow 64 while the portions 90, 92 are displaced inwardly toward each other in the direction of arrows 94 so as to engage the guidewire 12, 14. When the portions 90, 92 are displaced toward each other, a leg 91, secured to the portion 90 rides over the ratchet-like arrangement 96 as can be seen in FIG. 8A. However, the ratchet-like arrangement 96 is formed such that upon displacement of the mechanism 42E in a direction opposed to the arrow 64, such movement is inhibited if the portions 90, 92 are in positions inwardly toward each other. In such a case, the leg 91 engages the ratchet-like formation, thereby inhibiting rearward movement of the portion 90 while displaced toward portion 92. When the portions 90, 92 are displaced away from each other, as can be seen with reference to FIG. 8B, the leg 91 clears the ratchet-like arrangement 96 thereby permitting rearward movement, while the guidewire is in a disengaged condition. Accordingly, as can be seen in FIG. 8A, the actuator 42E is inhibited from engaging the guidewire 12, 14 when moved in a direction opposed to that indicated by arrow 64.

FIGS. 9-13 show further embodiments of an advancing device in accordance with the invention. The advancing device of FIG. 9 comprises an engaging mechanism 42E similar to the one shown in FIG. 8A having actuator 89, which comprises opposed portion 90, 92. The advancing device, having actuator 58, shown in FIG. 10 comprises any one of the engaging mechanisms 42A-42D. The advancing mechanism of FIG. 11 is similar to the advancing device shown in FIG. 10, save that it includes opposed tabs 97 which extend outwardly from the body 36 to facilitate manual operation of the device by enabling an operator to position his thumb and forefinger over the opposed tabs 97 so as to cause the operatively forward tab 97 to displace towards the operatively rearward tab 97 by the operator bringing his or her thumb and forefinger together.

FIGS. 12 and 13 show advancing devices in accordance with the invention which operate in a fishing-reel fashion. The operation of these advancing devices will be described in greater detail with reference to FIGS. 14, 16, and 17. The advancing device of FIG. 12 has an L-shaped handle 101 rotatable in the direction of arrow 100 to cause a trailing end portion of a guidewire to advance along the devices as indicated by arrow 102. The device of FIG. 13 works in similar fashion as the device in FIG. 12 save that it does not have an L-shaped handle but a dial formation 104.

Figure 14:
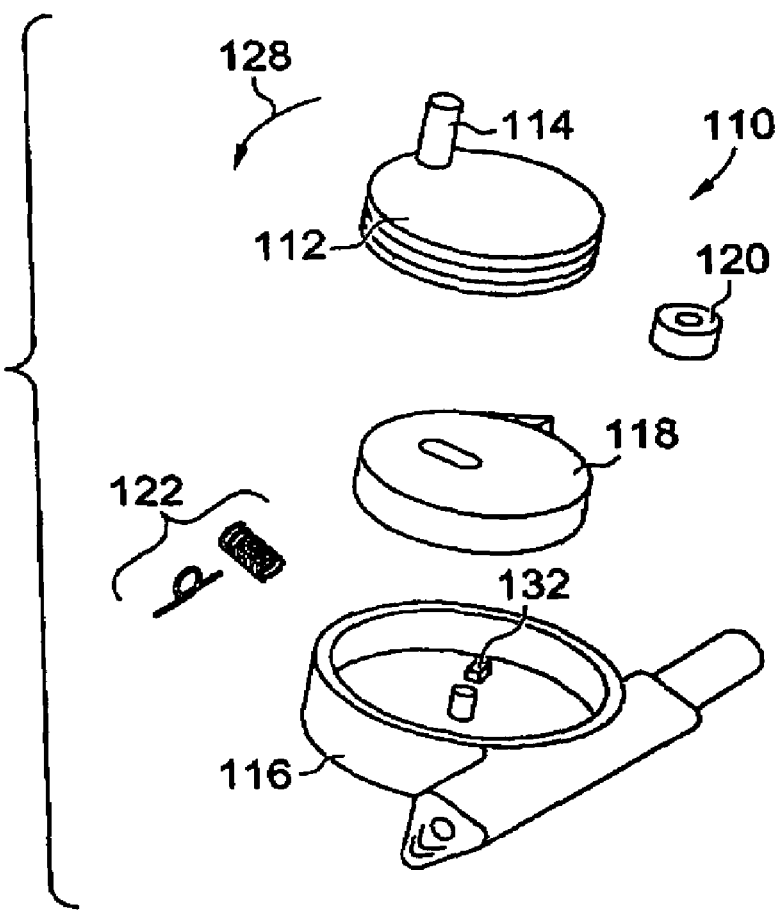
FIG. 14 shows a schematic exploded view of another advancing device in accordance with the invention.
Figure 15:
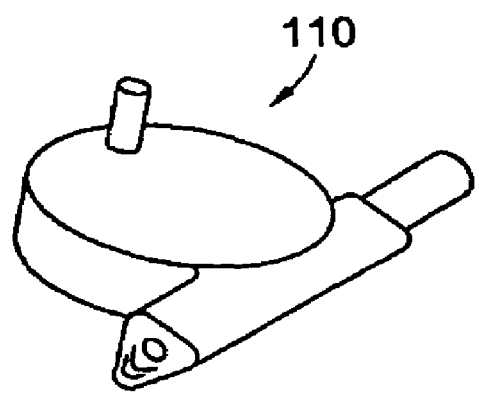
FIG. 15 shows a schematic three-dimensional view of the advancing device of FIG. 14, in an assembled condition.
Figure 17:
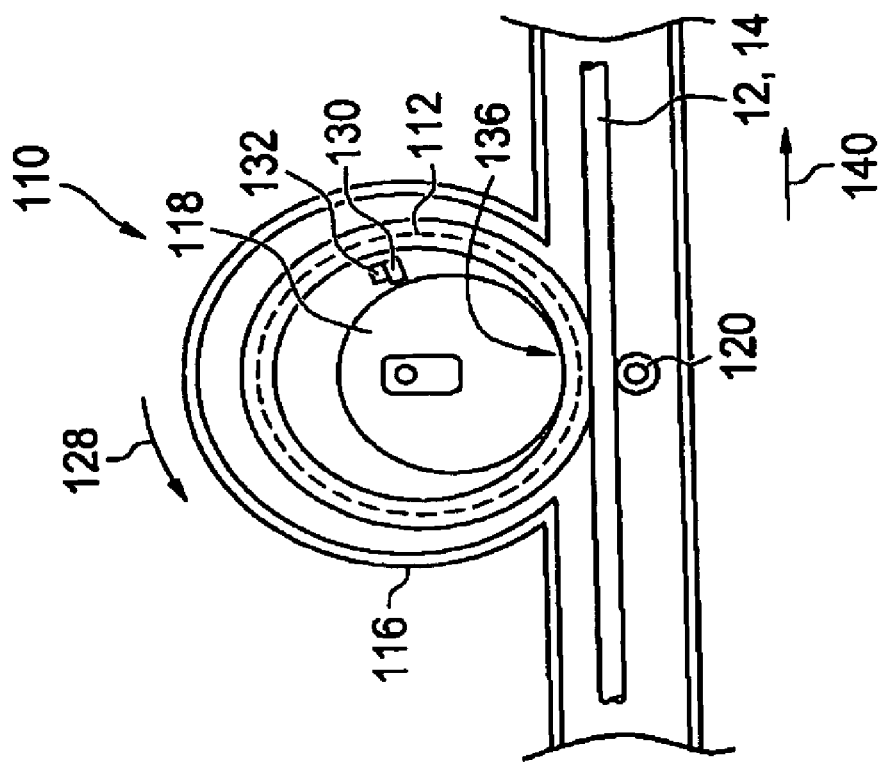
FIGS. 16 and 17 show schematic cross-sectional plan views of the device shown in FIGS. 14 and 15 indicating its operation.
Figure 16:
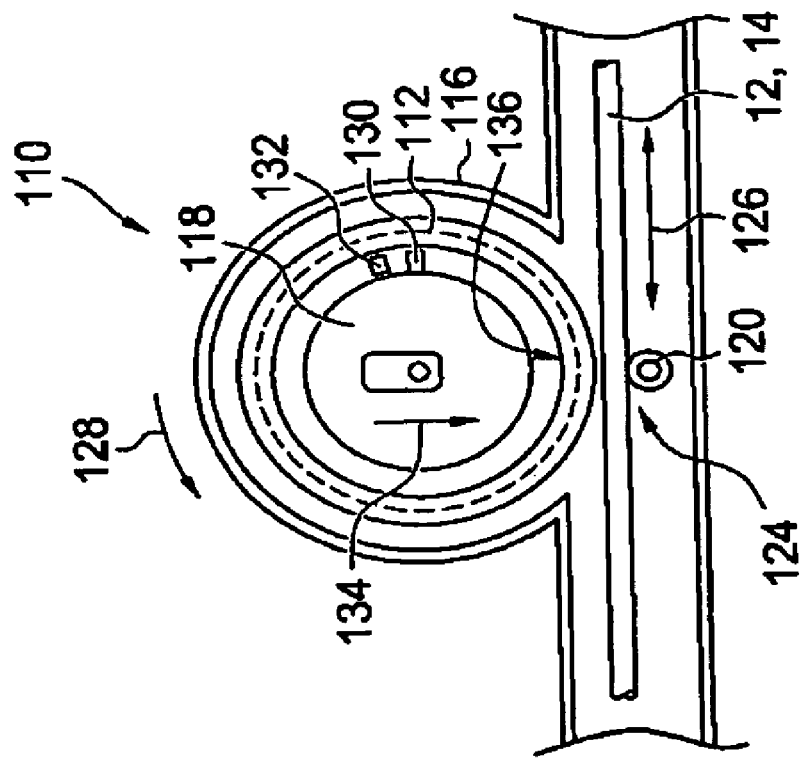

Referring now to FIG. 14, another embodiment of an advancing device in accordance with the invention is generally indicated by reference numeral 110. The device 110 works in similar fashion to the devices shown in FIGS. 12 and 13. The device 110 includes a pulley 112 with an inner surface 136 (FIGS. 16 and 17). The pulley 112 has an actuator in the form of a handle 114, which may be angularly displaced in the direction of arrow 128. Furthermore, the device 110 comprises a housing 116, a foot 130 (FIGS. 16 and 17), and a stop 132. It further includes a toggle member 118 operatively positioned between the pulley 112 and the housing 116. A pinch roller of the device 110 is indicated at 120. A suitable spring, as indicated at 122, is provided to urge the toggle member 118, and accordingly also the pulley 112, into a disengaged condition, in which the pulley 112 is disengaged from a guidewire, as will be described in greater detail hereinbelow. FIG. 15 shows the device 110 in an assembled condition.

Referring now to FIGS. 16 and 17, in which like reference numerals are used to designate similar parts unless otherwise stated, a method of operation of the device 10 will now be described. Referring initially to FIG. 16, the pulley 112 is shown in a disengaged position. In the disengaged position, clearance between the pulley 112 and the pinch roller 120, as indicated at 124, is sufficient to permit the guidewire 12, 14 to displace freely in the direction of arrows 126. It will be appreciated that an appropriate spring member 122, which is shown in Fig. 14, for example, urges the toggle member 118 into the position shown in FIG. 16, thereby to cause the pulley 112 to be in the disengaged position.

Referring now to FIG. 17, when the handle 114, as can best be seen with reference to FIG. 14, is angularly displaced in the direction of arrow 128, toggle member 118 is caused to displace angularly in the direction of arrow 128 also. As the toggle member 118 is urged to displace angularly in the direction of 128, a foot 130 on the toggle 118 comes into contact with a stop 132 on the housing 116. As the toggle member 118 is urged to displace further in the direction of arrow 128, toggle 118 pivots about the stop 132 so as to move in the direction of arrow 134, which is shown in FIG. 16, for example. As the toggle member 118 displaces in the direction of 134 it comes into contact with an inner surface 136 of the pulley 112 and urges it in the direction of arrow 134 also. As the toggle 118 displaces further, the pulley 112 is brought closer to the pinch roller 120 thereby to engage the guidewire 12, 14 between itself and the pinch roller 120. As the handle 114 continues to be displaced angularly, the pulley 112 causes the guidewire 12, 14 to be engaged between it and the pinch roller 120 so as to advance the guidewire 12, 14 in the direction of arrow 140 Typically, about 3 to 5 inches of guide wire is advanced every revolution of the pulley 112. When the handle 114 is then released, the spring 122 urges the toggle 118 back into the position shown in FIG. 16 thereby to release the pulley 112 from the guidewire 12, 14.

Figure 18:
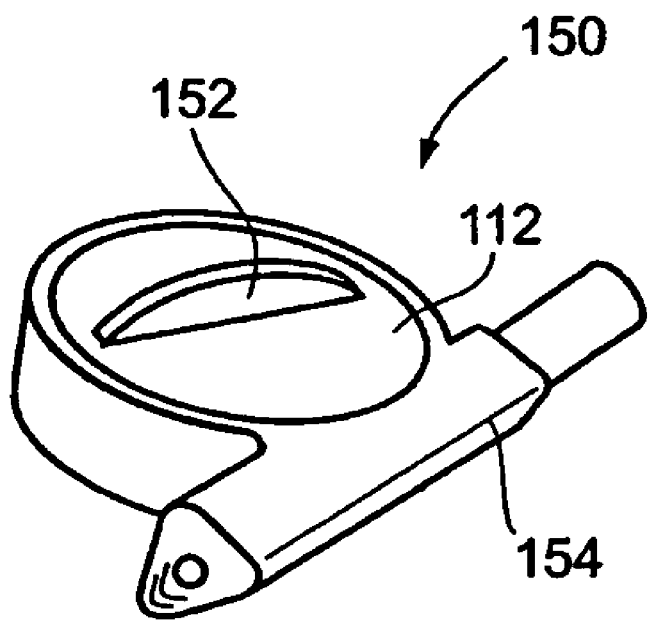
FIGS. 18 and 19 show schematic three-dimensional views of further embodiments of advancing devices.

Referring to FIG. 18, another embodiment of an advancing device in accordance with the invention is generally indicated by reference numeral 150. The device 150 functions in similar fashion to the device 110, which is shown in FIG. 14, for example. However, instead of an eccentric handle 114, the device 150 includes a flange 152 standing out from the pulley 112. The flange 152 is arranged to enable an operator to grip the flange dial-fashion between both sides. Furthermore, the device 150 comprises an elongate body portion 154. The elongate body portion 154 is cross-sectionally generally triangular in shape.

Figure 19:
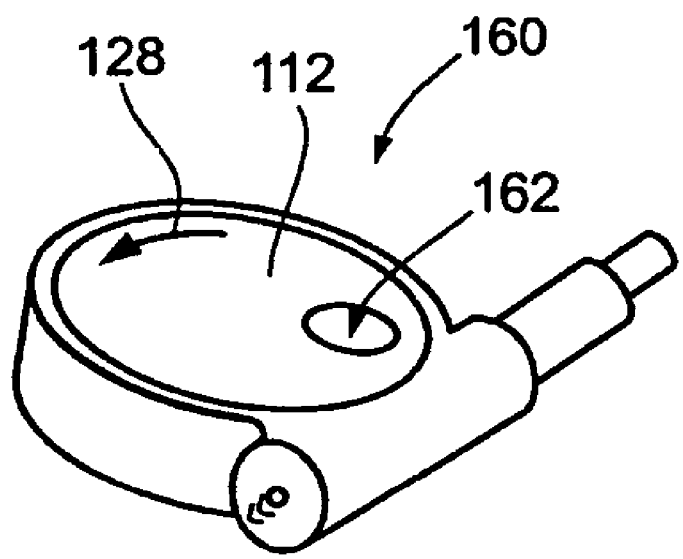

Referring to FIG. 19, another embodiment of an advancing device in accordance with the invention is generally indicated by reference numeral 160. The device 160 is similar to the device 110, which is shown in FIG. 14, for example, save that instead of an eccentric handle 114, the device 160 comprises an indent formation 162 to enable an operator to rotate the pulley 112 as indicated by arrow 128 by positioning a finger in the indent 162 and displacing his finger relative to the device 160 thereby to rotate the pulley 112.

Referring to FIGS. 20-25, further embodiments of an advancing device in accordance with the invention are generally indicated by reference numerals 170A-F. Advancing devices 170A-F operate in similar fashion to the device 18,20 shown in FIGS. 2 and 3.

The device 170A of FIG. 20 has a generally teardrop cross-sectional profile. The device 170B of FIG. 21 has a generally square-shaped cross-sectional profile. The device 170C of FIG. 22 has a generally triangular-shaped cross-sectional profile. The device 170D of FIG. 23 has a generally horizontally oval-shaped cross-sectional profile. The device 170E of FIG. 24 has a generally vertical oval-shaped cross-sectional profile. The device 170F of FIG. 25 has a generally horizontal oval-shaped cross-sectional profile.

Furthermore, the device 170F has a thumb grip formation 172 and an actuator 174 which comprises a ring-shaped formation 176 to enable the device 170F to be operated by positioning a finger in the ring formation 176 and a thumb of the same hand against the thumb formation 172. The actuator 174 is then displaced relative to the body by the operator moving his finger toward his or her thumb.

Figure 26:
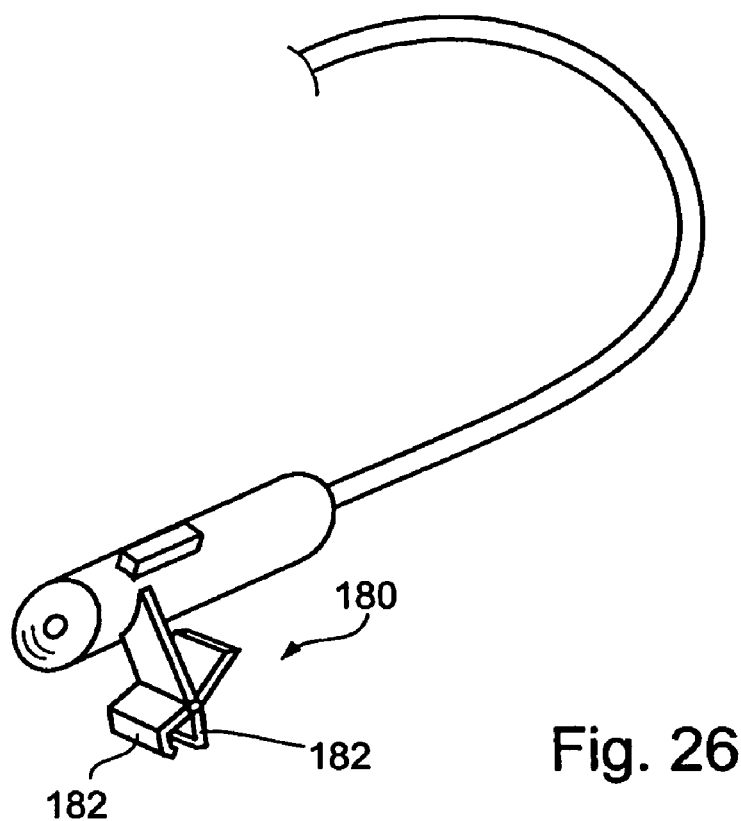
FIG. 26 shows a schematic three-dimensional view of an advancing device in accordance with the invention having a clamping arrangement.

Referring now to FIG. 26, any one of the advancing devices herein described can comprise a clamping arrangement, as indicated by reference numeral 180 in FIG. 26. The clamping arrangement 180 can be in any appropriate form. In the form shown in FIG. 26, the clamping arrangement 180 is in the form of a clamp-like formation defining opposed jaws 182. In use, the jaws can be clamped to a covering on the support 16 of FIG. 1 so as to retain the device in position. Accordingly, with reference to FIG. 1, securing devices 30, 32 can be in the form of the clamping arrangements of FIG. 26. Conveniently, the clamping arrangement of FIG. 26 can include a suitable urging member, such as a spring, to urge the jaws 182 into a closed condition.

Figure 27:
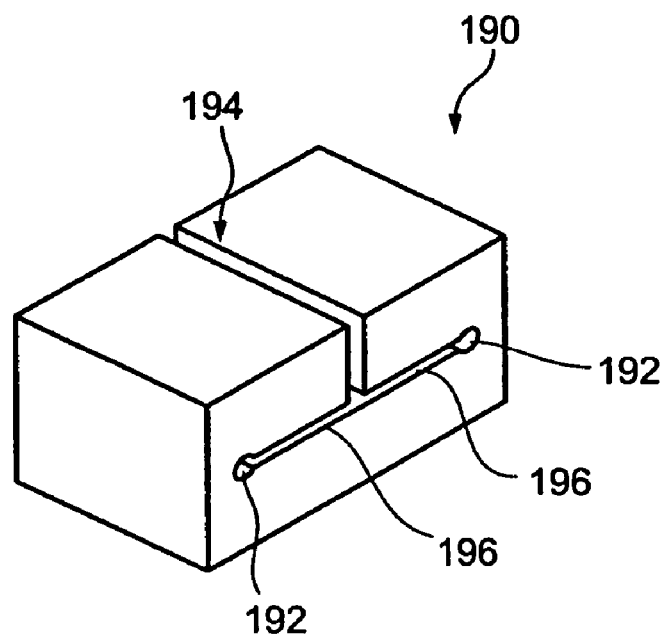
FIG. 27 shows a schematic three-dimensional view of a guide block, in accordance with the invention, for locating two guidewires during the course of a surgical procedure.

Referring now to FIG. 27, another embodiment of a guide block, similar to the guide block 34 in FIG. 1, is shown at 190. The guide block 190 comprises opposed channels 192. The channels 192 are linked to a slot 194 by means of slots 196. The block 190 is typically in the form of a resilient material such as silicone, or a synthetic plastics material, or the like. In use, opposed guidewires can be positioned in the channels 192 in similar fashion to that shown in FIG. 1. To position the guidewires, the block 190 can be flexed so as to open the slots 194, 196 so as to ease the positioning of the guidewires in the channels 192. Once inside the channels 192, the block 190 can be positioned on the support 16 of FIG. 1, so as to guide the guidewires as already described with reference to FIG. 1.

Typically, in use, the guide wires are introduced into the patient and the trailing end portions are then located in the block 34 (FIG. 1), 190 (FIG. 27). The person performing the medical procedure can take note of which trailing end portion, located in which channel of the block 34, 190, corresponds with which leading end portion. Thereafter, the trailing end portions of the guide wires can be advanced through the advancing devices so as to be contained in the containers. Instead, the guide wires can initially be advanced into the containers by means of the advancing devices, and can then be withdrawn from the containers to introduce the leading end portions into the patient.

Figure 28:
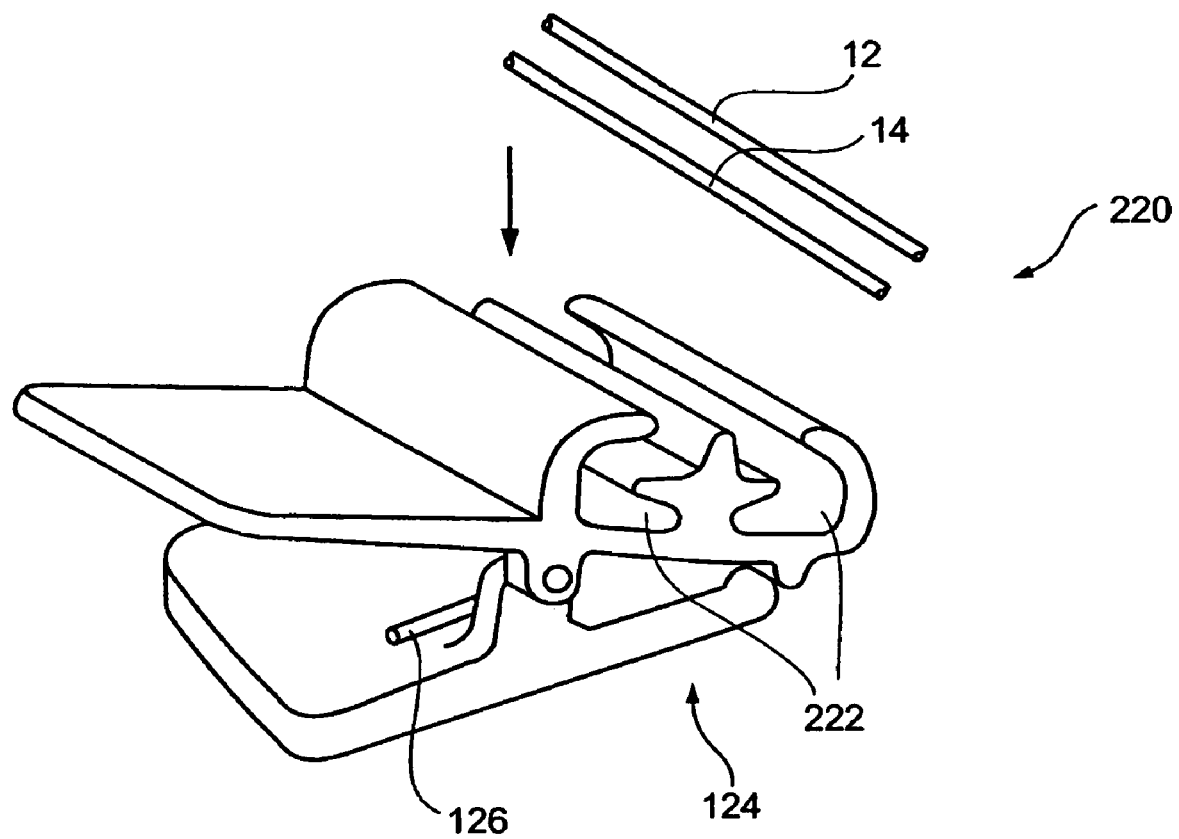
FIG. 28 shows a schematic three-dimensional view of a clamp, in accordance with the invention, arranged to guide two guidewires during the performance of a medical procedure.

Referring now to FIG. 28, instead of a block, 34 (FIG. 1), 190 FIG. 27), a clamping arrangement 220 can be used. The clamping arrangement 220 defines opposed channels 222 in which opposed guidewires 12, 14 can be received. Furthermore, the clamping arrangement 220 comprises a jaw-like arrangement at 124 for clamping it to a cover on the support 16 of FIG. 1. A suitable biasing member, such as a spring 126, can be provided to urge the jaw-like arrangement 124 into a closed condition.

Figure 29:
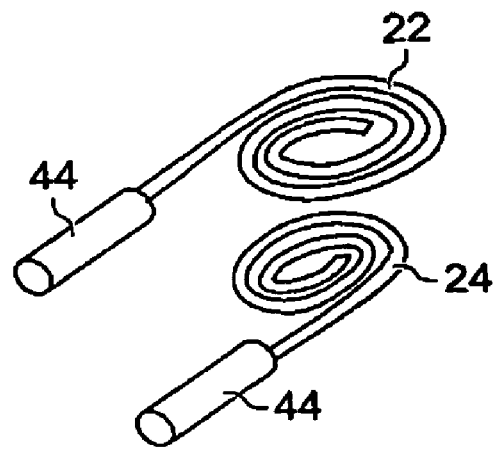
FIG. 29 shows a schematic three-dimensional view of two advancing devices in accordance with the invention, each of which has a disposable loop, in which a guidewire is normally packaged, releasably mounted thereon.

As mentioned with reference to FIGS. 1-3, the advancing device of the invention comprises a mounting formation, indicated by reference numeral 44, which is arranged to enable an end of a protective loop in which a guidewire is normally packaged to be releasably mounted thereon. Referring to FIG. 29, when two guidewires are to be used in a medical procedure, the protective loops 22, 24 of each guidewire can be releasably mounted on the mounting formations 44 of two advancing devices in accordance with the invention as indicated in FIG. 29. The protective loops can be held in position by means of a clamp. Guidewires are normally prepackaged with clamps which retain the protective loops in coiled configurations. Advantageously, the same clamp with which a guidewire is normally packaged can be used during the medical procedure to retain the protective loops in a coiled configuration. The clamps can also be used to clamp the two protective loops together.

Figure 30:
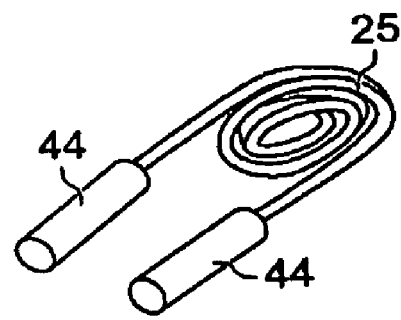
FIG. 30 shows a schematic three-dimensional view of two advancing devices in accordance with the invention, and opposed end portions of a single disposable loop, in which a guidewire is normally packaged, mounted on the advancing devices.

Referring to FIG. 30, and where two guidewires are used in a medical procedure, instead of releasably mounting an end portion of a protective loop on each of the advancing devices, a single protective loop 25 can be used. In such a case, an opposed end portion of the protective loop can be releaseably mounted on the formations 44 of both devices.

Figure 31:
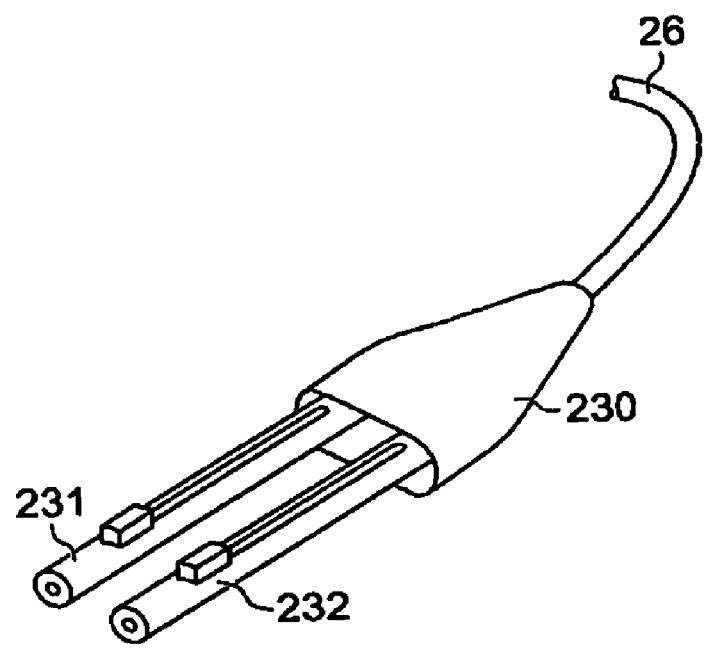
FIG. 31 schematically shows two advancing devices in accordance with the invention and an arrangement for guiding trailing end portions of two guidewires advanced by means of the advancing devices into a common disposable loop, in which disposable loop a guidewire is normally packaged.

Referring now to FIG. 31, a single protective loop 26 can be used to serve two or more advancing devices 231, 232. In such a case, a suitable guide 230 can be provided.

Conveniently, the advancing devices described above can be made to be disposable. In such a case, they can be supplied in pre-packaged sterilized form. In addition, they can be designed with a predetermined life expectancy, such as, to perform at least 15 strokes in the case of the embodiments which perform strokes, or to cause at least 60 inches of travel of the guide wire in the case of the embodiments having pulleys, for example. Instead, the advancing devices can be made to be sterilizable repeatedly so as to permit repeated use. Advantageously, the devices are designed to be resistant to typical operating conditions. Accordingly, the devices can be designed so that their operation would not be impaired if exposed to blood, saline solutions, or if particles typically present during the medical procedure intrude into the bodies of the devices, and the like. Where appropriate, the devices can be made from Nylon, ABS, silicone, Delrin, Polycarbonate, urethane, SST, or the like. The advancing devices can include parts which are snap fitted together. Instead, or in addition, the advancing devices can include parts which are secured together with conventional fasteners, such as screws, rivets, and/or the like, or by making use of appropriate adhesives.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of performing a medical procedure on a living body, the method comprising:
    inserting a leading end portion of a guidewire into the living body; and
    advancing a trailing end portion of said guidewire through an advancing device and into a container, said container being arranged to coil said trailing end portion of said guidewire as said trailing end portion is advanced into said container, wherein said advancing device comprises a device body and an engaging mechanism, wherein advancing the trailing end portion includes:
    applying a force to an engaging mechanism only in an axial direction toward the container to engage the guidewire with the engaging mechanism and to provide movement of the guidewire into the container; and
    releasing the engaging mechanism to enable the engaging mechanism to automatically disengage from the guidewire and to move in a direction axially away from the container without moving the guidewire.

2. The method of claim 1, wherein said guidewire is packaged in a protective loop, the method comprising removing said guidewire from said protective loop prior to inserting said leading end portion of said guidewire into the living body and advancing said trailing end portion of said guidewire into the container.

3. The method of claim 2, wherein said container is the protective loop, and wherein advancing said trailing end portion of the guidewire into said container comprises advancing said trailing end portion of the guidewire into said protective loop.

4. The method of claim 1, wherein inserting said leading end portion of the guidewire into the living body comprises inserting said leading end portion into a lumen of the living body.

5. The method of claim 4, wherein said lumen forms part of a vasculature of the living body, and wherein inserting said leading end portion into said lumen comprises inserting said leading end portion through a hemostasis valve leading into the vasculature.

6. The method of claim 1, wherein said container is mounted on an advancing device, and wherein advancing said trailing end portion of the guidewire into said container comprises passing an end of said trailing end portion of the guidewire through said advancing device and operating said advancing device to cause said advancing device to advance said trailing end portion of the guidewire into said container.

7. The method of claim 1, further comprising releasably mounting said container on said advancing device.

8. The method of claim 7, wherein the guidewire is packaged in a protective loop, the method comprising removing said guidewire from said protective loop prior to inserting said leading end portion of the guidewire into the living body and advancing said trailing end portion of the guidewire into said container.

9. The method of claim 8, wherein said container is the protective loop, and wherein releasably mounting said container on said advancing device comprises releasably mounting an end portion of said protective loop on said advancing device.

10. The method of claim 1, wherein said engaging mechanism of said advancing device is arranged to be disengaged from the guidewire when said advancing mechanism is not being operated.

11. The method of claim 1, wherein said engaging mechanism comprises at least one engaging member which engages the guidewire in response to operating said advancing device, the method comprising causing said engaging member to displace from a disengaged position, clear of the guidewire, to an engaged position, in which it engages the guidewire, in response to operating said advancing device.

12. The method of claim 11, wherein the engaging member is arranged to translate relative to the device body while in engagement with the guidewire in response to operating said advancing device, thereby to cause said trailing end portion of the guidewire to advance relative to the device body and into the container.

* * * * *

UNITED STATES PATENT AND TRADEMARK OFFICE
CERTIFICATE OF CORRECTION

PATENT NO.         : 7,544,170 B2
APPLICATION NO. : 10/420770
DATED              : June 9, 2009
INVENTOR(S)        : Eric B. Williams et al.

It is certified that error appears in the above-identified patent and that said Letters Patent is hereby corrected as shown below:

Column 12
Line 11, delete "mounted on an advancing", and insert therefor --mounted on the advancing--.

Line 36, delete "at least one", and insert therefor --an--.

Line 47, delete "the", and insert therefor --said--.

Signed and Sealed this

Fifteenth Day of September, 2009

David J. Kappos
*Director of the United States Patent and Trademark Office*